United States Patent [19]

Robey

[11] 4,426,536
[45] Jan. 17, 1984

[54] SYNTHESIS OF PHENYLACETIC ACID ESTERS

[75] Inventor: Roger L. Robey, Greenwood, Ind.

[73] Assignee: Eli Lilly and Company, Indianapolis, Ind.

[21] Appl. No.: 387,910

[22] Filed: Jun. 14, 1982

[51] Int. Cl.$^3$ ............................................. C07L 69/76
[52] U.S. Cl. ...................... 560/105; 560/20; 560/23; 560/55; 560/73; 560/106; 260/465 R; 568/332
[58] Field of Search ................. 560/105, 106, 20, 23, 560/55, 73

[56] References Cited

FOREIGN PATENT DOCUMENTS 760968 6/1971 Belgium .

OTHER PUBLICATIONS

*Organic Reactions*, vol. 24, p. 240.
Dombrovskii and Naidan, *J. Org. Chem. U.S.S.R. 32,* 1256–58, (1962).
Dombrovskii and Naidan, *J. Org. Chem. U.S.S.R. 34,* 1474–77, (1964).
Hill, *J. Org. Chem. 25,* 1115–18, (1960).
Nakamo et al., *J. Chem. Soc. Chem. Comm.,* 808–09, (1977).
Cadogan and Duell, *J. Chem. Soc.,* 4154–4157, (1962).
Kharasch et al., *J. Org. Chem. 18,* 328–32, (1953).
Kharasch et al., *J. Am. Chem. Soc. 69,* 1100–05, (1947).
Hilgetag and Martini, *Preparative Organic Chemistry,* John Wiley and Sons, New York, 1972, p. 341.
Wakselman and Molines, *Synthesis* 622–23, (1979).
Kharasch et al., *J. Am. Chem. Soc. 69* 1105–10, (1947).
Kimoto and Cohen, *J. Org. Chem. 45,* 3831–35, (1980).
Hill et al., *J. Org. Chem. 30,* 411–15, (1965).
Smith et al., *Synthesis* 493–95, (1980).

*Primary Examiner*—Paul J. Killos
*Attorney, Agent, or Firm*—Joseph A. Jones; Arthur R. Whale

[57] ABSTRACT

Esters of phenylacetic acids are prepared in a single step by hydrolysis of 2,2,2-trichloro-1-phenylethanes in inorganic basic media.

14 Claims, No Drawings

SYNTHESIS OF PHENYLACETIC ACID ESTERS

BACKGROUND OF THE INVENTION

1. Field of the Invention

This invention belongs to the field of synthetic organic chemistry, and provides a process for the synthesis of esters of phenylacetic acids in a single step from 2,2,2-trichloro-1-phenylethanes.

2. State of the Art

The hydrolysis of trichloromethyl compounds to form carboxylic acids and derivatives thereof is well known. For example, Belgian Pat. No. 760,968 shows the formation of 3-trifluoromethylphenylacetic acid from the corresponding 2,2,2-trichloroethane by hydrolysis with potassium hydroxide in ethylene glycol. Dombrovskii and Naidan, *J. Org. Chem. U.S.S.R.* 32, 1256–58 (1962), prepared phenylacetic acid by hydrolyzing 2,2,2-trichloro-1-phenylethane with lead nitrate in acetic acid, and the same authors, *J. Org. Chem. U.S.S.R.* 34, 1474–77 (1964), prepared phenylacetic acid and 4-nitrophenylacetic acid by hydrolyses with mercuric oxide, or with sulfuric acid.

Various trichloromethylbenzene compounds have been hydrolyzed to the corresponding acid chlorides, for example with ferric chloride and with siloxanes. Hill, *J. Org. Chem.* 25, 1115–18 (1960), and Nakamo et al., *J. Chem. Soc. Chem. Comm.*, 808–09 (1977).

Other aryltrichloromethyl compounds have been hydrolyzed to the corresponding acids with perchloric acid in acetic acid, and cuprous chloride in hydrochloric acid. Cadogan and Duell, *J. Chem. Soc.*, 4154–57 (1962); Kharasch et al., *J. Org. Chem.* 18, 328–32 (1953); Kharasch et al., *J. Am. Chem. Soc.* 69, 1100–05 (1947).

There is some precedent in the literature for the formation of carboxylic acid esters from trichloromethane compounds. One system proceeds by reactions with sodium alkoxides, as taught by Hilgetag and Martini, Preparative Organic Chemistry, John Wiley and Sons, New York, 1972, page 341; Wakselman and Molines, Synthesis 622–23 (1979); and Kharasch et al., *J. Am. Chem. Soc.* 69, 1105 (1947). The process is acceptable with alkyl compounds, but is not satisfactory for phenylethane derivatives.

Esters have also been prepared by a process which proceeds through ortho-ester intermediates, as shown by Kimoto and Cohen, *J. Org. Chem.* 45, 3831–35 (1980), who worked with 2-trifluoromethylimidazoles and converted them to the corresponding 2-(carbomethoxy)imidazoles, proceeding through the trimethoxymethane intermediate, and Hill et al., *J. Org. Chem.* 30, 411–15 (1965), who converted benzotrichlorides to orthobenzoates with metal halides such as aluminum chloride and ferric chloride. The phenylethanes which are starting compounds of the present invention are inert to these conditions; the imidazole starting compounds of Kimoto, in particular, are quite unique because of the tautomerism of their double bonds.

Finally, Smith et al., *Synthesis* 493–95 (1980), prepared the t-butyl ester of a complexly substituted pyrrole-2-carboxylic acid by reacting the corresponding 2-trichloromethylpyrrole with t-butanol and sodium acetate.

SUMMARY OF THE INVENTION

The present invention provides a process for preparing a phenylacetate of the formula

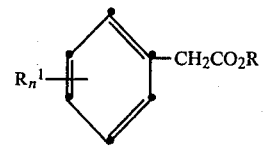

wherein
R is $C_1$–$C_6$ primary or secondary alkyl or $C_3$–$C_6$ cycloalkyl; the $R^1$ groups are independently chloro, fluoro, bromo, iodo, $C_1$–$C_3$ alkyl, $C_1$–$C_3$ alkoxy, nitro, or trifluoromethyl;
n is 0–3, provided that n is 3 only when the $R^1$ groups are chloro or bromo;
comprising hydrolysing a trichloro compound of the formula

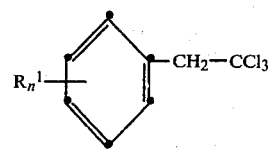

with sodium or potassium hydroxide in the presence of an alcohol of the formula ROH.

DESCRIPTION OF THE PREFERRED EMBODIMENTS

In this document, all temperatures are expressed in degrees Celsius.

The general chemical terms in the above description are used as they usually are in organic chemistry. The terms $C_1$–$C_3$ alkyl, $C_1$–$C_3$ alkoxy, $C_3$–$C_6$ cycloalkyl and $C_1$–$C_6$ primary or secondary alkyl refer to groups such as methyl, ethyl, isopropyl, methoxy, propoxy, butyl, pentyl, neopentyl, 2-methylpentyl, hexyl, 2-methylbutyl, 1-ethylbutyl, cyclopropyl, cyclopentyl, cyclohexyl and the like.

Starting compounds used in the process of this invention are readily obtained commercially, or prepared by methods commonly known to organic chemists.

It is believed that the phenylacetates prepared by the present invention are easily understood, but a group of representative compounds will be specifically named to assure comprehension.

Methyl (2-chlorophenyl)acetate
Ethyl (4-fluorophenyl)acetate
Propyl (3-bromophenyl)acetate
Isopropyl phenylacetate
Butyl (3-iodophenyl)acetate
s-Butyl (4-methylphenyl)acetate
Pentyl (3-isopropylphenyl)acetate
1-Methylbutyl (2-ethoxyphenyl)acetate
2-Methylbutyl (3-propoxyphenyl)acetate
Hexyl (4-nitrophenyl)acetate
2-Ethylbutyl (4-trifluoromethylphenyl)acetate
3-Methylpentyl (2,4,6-tribromophenyl)acetate
Cyclopropyl (3-bromo-2,5-dichlorophenyl)acetate
Cyclobutyl (3,4,5-trichlorophenyl)acetate
Cyclopentyl (2,6-dichloro-4-bromophenyl)acetate
Cyclohexyl (3-ethyl-2-fluorophenyl)acetate
Neopentyl (4-iodo-2-nitrophenyl)acetate
Isobutyl (3-fluoro-4-trifluoromethylphenyl)acetate
Hexyl (2-propyl-4-trifluoromethylphenyl)acetate
Methyl phenylacetate Methyl (3-chloro-4-ethoxyphenyl)acetate
Cyclohexyl (3-methoxy-2-methylphenyl)acetate
Propyl (2-chloro-6-trifluoromethylphenyl)acetate
Pentyl (2-ethyl-4-ethoxyphenyl)acetate
2-Ethylbutyl (2-bromo-4-nitrophenyl)acetate
Isopropyl (4-fluoro-2-methylphenyl)acetate
Ethyl (2,4-dichloro-5-bromophenyl)acetate The most preferred products of the present process are those wherein $R^1$ is 3-trifluoromethyl. Further preferred classes of products are those wherein R is $C_1$-$C_4$ alkyl, wherein R is primary alkyl, especially $C_1$-$C_4$ primary alkyl, and still more particularly is methyl or butyl. Still other classes of preferred products are those wherein n is 1, wherein the $R^1$ substituent is at the 3-position, and wherein $R^1$ is halo, especially chloro, fluoro or bromo. Still another class of preferred products includes those compounds wherein n is 2 and $R^1$ is chloro or bromo.

The process of this invention is carried out simply by combining the trichloro starting compound with potassium or sodium hydroxide in the presence of an adequate amount of the alcohol which provides the desired R group, and preferably but not necessarily in the presence of a small amount of water. The preferred hydroxide is potassium hydroxide, and it has been found that the quantity of water which is normally present in commercial potassium hydroxide, about 15% of the amount of the base, is quite desirable. In general, amounts of water in the range of from about 5 to about 20% of the amount of the hydroxide may be used as is convenient in the circumstances. Larger amounts of water may also be used if convenient, even up to an amount equal to the amount of the hydroxide.

It is advisable to use a large excess of the hydroxide. In general, amounts of the hydroxide from about 5 moles to about 20 moles or more of hydroxide per mole of starting compound are appropriate. The preferred amount is from about 6 to about 12 moles of hydroxide per mole of starting compound, most preferably about 10 moles.

It is most convenient to operate the process by using the alcohol as the solvent for the process. Accordingly, a large excess of the alcohol will normally be present. Such operation is convenient in that it is unnecessary to provide and recover a second solvent, and the large excess of alcohol provides high reaction rates.

However, if it is desired in a given instance, the process can be operated in an inert organic solvent, and smaller amounts of the alcohol may accordingly be used. For example, such inert organic solvents as aromatics, such as benzene, toluene or a xylene, haloaromatics such as chlorobenzene or a chlorotoluene, halogenated alkanes such as dichloromethane, alkanes such as pentane, a hexane or an octane and the like, and ethers such as diethyl ether, diisopropyl ether and tetrahydrofuran are quite appropriate inert reaction solvents. When the process is operated in such a manner, fairly large excesses of the alcohol are quite appropriate. For example, an amount of alcohol in the range of from about 5 to about 10 moles per mole of starting compound will assure that the more expensive starting compound is fully consumed. Larger excesses may be used if desired, of course.

The temperature of the process, most preferably and conveniently, is about the reflux temperature of the mixture at ambient pressure. In general, ambient temperature reaction rates are inconveniently slow. It is preferable to operate the process at a temperature in the range of from about 50° to about 150°. The optimum operating temperature for a given reaction is easily found according to the routine skill of organic chemists. The process may be operated under a partial vacuum, but it is ordinarily disadvantageous to do so. It may often advantageously be operated under pressure, in order to raise the boiling point of the reaction mixture and allow higher operating temperatures and thus a faster reaction rate.

The necessary reaction time, of course, is a function of the starting materials and the operating temperature. The optimum reaction time for a given process is, as always, a compromise which is found by taking into account the competing goals of maximum throughput, which is favored by short reaction times, and maximum yield, which is favored by long reaction times.

As is illustrated by the examples below, the process of this invention gives quite unexpectedly high yields of the ester in a single step, although a chemist would expect that the basic hydrolysis of this process would give primarily or entirely the carboxylic acid, and the esterification would have to be done in a second step.

Not only does the process give excellent yields of the desired ester, but the residue left after the process, in fact, consists largely of the corresponding carboxylic acid, which may be esterified by making the reaction mixture acid with an aqueous mineral acid, preferably sulfuric acid, and heating it briefly at an elevated temperature as described above. Thus, it is preferred to post-treat the reaction mixture from this invention by making it acid and heating it to assure that the unreacted portion of the starting material is fully consumed. Examples below illustrate the point.

The ester obtained from the product of this invention is readily isolated by making the reaction mixture acid with any strong, preferably inexpensive, aqueous acid, and isolating the ester from the organic layer according to ordinary procedures. For example, the organic layer may be dried over a hygroscopic inorganic salt, and evaporated to remove the remaining alcohol or other solvent. The recovered ester usually need not be purified for use as an intermediate.

The esters prepared by the present process, except for those in which n is 3, are preferably used as intermediates for preparing a series of herbicides disclosed by H. M. Taylor in U.S. Pat. No. 4,152,136. The herbicides are 4-pyridones having a phenyl ring, usually substituted, at the 3-position. The esters are converted to the preferred intermediate used by Taylor by a simple process illustrated in the preparations below. The ester is first reacted with phenylacetonitrile, preferably in the presence of a strong base such as sodium methoxide at a relatively high temperature. The resulting intermediate, a 1-cyano-1,3-diphenyl-2-propanone, is then hydrolyzed in an acid medium, for example in a mixture of sulfuric acid and acetic acid, to remove the nitrile group and prepare the desired 1,3-diphenyl-2-propanone which Taylor uses as a preferred starting compound for his 4-pyridones. It will be understood that the $R^1$ group or groups of the ester prepared by the process of this invention carries through and is present on the corresponding phenyl ring of the herbicide.

The esters wherein n is 3 are outside Taylor's scope. These compounds are herbicides, as is taught by the plant science literature, e.g., U.S. Pat. No. 3,163,516, of Well and Sanford.

The following examples illustrate the process according to the present invention, and the preparations which follow them show the use of esters so prepared as intermediates.

Example 1

Butyl (3-trifluoromethylphenyl)acetate

Fifty ml. of butanol was added to 11.2 g. of potassium hydroxide, reagent grade, containing about 14% of water, and the mixture was stirred until most of the potassium hydroxide had dissolved. To the mixture was then added 5.6 g. of 1,1,1-trichloro-2-(3-trifluoromethylphenyl)ethane, dropwise over a period of 5 minutes. The mixture warmed exothermically to about 35° as the addition was made. The mixture was then heated to reflux, about 115°, and was stirred under reflux for 6 hours, cooled to ambient temperature and allowed to stand for about 3 days. It was then poured into 60 ml. of 5 N sulfuric acid, and the layers were separated. The lower, aqueous layer was extracted with about 50 ml. of dichloromethane, the organic portion was combined with the upper, organic layer, and the combined organics were washed with 20 ml. of 1 N sodium hydroxide and dried over sodium sulfate. The volatile portions were evaporated under vacuum to obtain 4.3 g. of crude product.

The sodium hydroxide wash was made acid with dilute sulfuric acid, and was extracted with about 35 ml. of dichloromethane. The organic layer was dried over sodium sulfate and evaporated under vacuum to obtain 0.7 g. of an oil.

The major product was identified as being the desired product by its nuclear magnetic resonance spectrum, run in $CDCl_3$ on a 60 mHz instrument, which showed the following characteristic features:

$\delta 0.8-1.2$ (3H, m), 1.2-1.7 (4H, m), 3.7 (2H, s), 4.2 (2H, t), 7.5 (4H, m).

The major product was further purified by distillation at 72°-80° under 0.05 torr, which provided 3.5 g. of pale yellow oily product. No residue was left in the distillation flask after the distillation.

The product was further identified by its infrared spectrum, which showed a strong absorption band at 1730 cm.$^{-1}$, and only a trace of a band at 1640 cm.$^{-1}$, which, if present, would indicate the possible 2-chloro-2-butoxystyrene by-product.

Example 2

Butyl (3-trifluoromethylphenyl)acetate

To 200 ml. of butanol was added 40.3 g. of potassium hydroxide containing about 14% of water, and the mixture was stirred at ambient temperature to obtain a gelatinous mixture. To it was added 20 g. of 1,1,1-trichloro-2-(3-trifluoromethylphenyl)ethane, over about 5 minutes. The mixture was then heated to reflux and stirred at that temperature for 5 hours. It was then cooled and worked up as described in Example 1 above. The major product was distilled at 89°-97° under 0.5-0.7 torr to obtain 12.8 g. of the desired product. It was analyzed by vapor phase chromatography, using a 180-cm. column packed with Chrom G silica gel coated with 1.5% of OV-17 and 1.95% of OV-210, and found to be 94.0% pure.

Example 3

Butyl (3-trifluoromethylphenyl)acetate

The process of Example 1 was followed on a larger scale, using 80.7 g. of potassium hydroxide and 40 g. of the trichloroethane in 340 ml. of butanol. The major product amounted to 33.3 g. of crude oil, which was distilled at 112° under 3 torr to obtain 26.1 g. of purified product, which was 98.1% pure by vapor phase chromatography.

Example 4

Butyl (2-chlorophenyl)acetate

Forty ml. of butanol was added to 9.2 g. of potassium hydroxide, which contained about 14% water, and was stirred at ambient temperature for 1 hour. To the mixture was added in one portion, 4 g. of 1,1,1-trichloro-2-(2-chlorophenyl)ethane. The mixture was heated to reflux and stirred at that temperature for 6 hours, and was cooled overnight to ambient temperature. It was then poured into 125 ml. of 1 N hydrochloric acid and stirred at ambient temperature for 30 minutes. The layers were then separated, and the aqueous layer was washed twice with about 60 ml. portions of diethyl ether. The organics were combined, and washed with two 25 ml. portions each of 10% sodium bicarbonate solution, water, and saturated sodium chloride solution. The washed organic portion was then dried over sodium sulfate, filtered and evaporated under vacuum to obtain 3.23 g. of crude product, which was found to be 87.6% pure by chromatography. A 2.5 g. portion of the above was distilled at 135° and 8 torr to obtain 1.9 g. of purified product, 97.0% pure by chromatography.

Example 5

Butyl phenylacetate

The process of Example 4 was followed, using 45 ml. of butanol, 12.5 g. of potassium hydroxide, and 4.6 g. of 1,1,1-trichloro-2-phenylethane. The reflux was carried on for 8 hours, at 110°. The product was 3.85 g. of rather impure oil, apparently containing some of the 2-chloro-2-butoxystyrene impurity, which was converted to desired product by adding 8 ml. of butanol and 40 ml. of 1 N hydrochloric acid and stirring the mixture for 20 minutes. The layers were separated, and the aqueous was extracted with two 30 ml. portions of diethyl ether. The organics were combined and washed with saturated sodium chloride solution, dried over sodium sulfate and evaporated under vacuum to obtain 4.2 g. of partially purified product, 77% pure by vapor phase chromatography.

Example 6

Butyl (3-chloro-2-methylphenyl)acetate

To 10.9 g. of potassium hydroxide of the same grade used in the examples above was added 50 ml. of butanol, and the mixture was stirred for 1 hour. To it was added 5.0 g. of 1,1,1-trichloro-2-(3-chloro-2-methylphenyl)ethane, and the mixture was stirred under reflux at 115° for 6 hours and allowed to cool overnight to ambient temperature. The mixture was then worked up as described in Example 4 above to obtain 4.5 g. of crude product as the major product. It was then taken up in 15 ml. of butanol and stirred with 40 ml. of 1 N hydrochloric acid at ambient temperature for 30 minutes. The layers were then separated, extracted and dried as described in Example 5 above to obtain 3.41 g. of product, found to be 92% pure by vapor phase chromatography.

Example 7

Butyl (2,4,6-trichlorophenyl)acetate

A 9.0 g. portion of potassium hydroxide of the grade described in the examples above was combined with 50 ml. of butanol, and the mixture was stirred for 15 minutes. To it was added 5 g. of 1,1,1-trichloro-2-(2,4,6-trichlorophenyl)ethane, and the mixture was stirred under reflux at 115° for 7 hours. It was then cooled to ambient temperature overnight, and worked up substantially as described in Example 4 above to obtain 3.9 g. of product, 96% pure by vapor phase chromatography. The product was distilled at 155°–162° under 0.35 torr to obtain 3.4 g. of purified product.

The following examples illustrate syntheses according to the present invention wherein the by-product carboxylic acid is consumed by an acid reflux step after the completion of the process of this invention.

Example 8

Butyl (3-trifluoromethylphenyl)acetate

To 5.6 g. of potassium hydroxide of the grade described above was added 25 ml. of butanol, and the mixture was stirred for 15 minutes. To it was added dropwise 2.8 g. of 1,1,1-trichloro-2-(3-trifluoromethylphenyl)ethane, and the mixture was stirred under reflux for 3.75 hours. It was then cooled to 5°, and to it was added dropwise 6 ml. of concentrated sulfuric acid. The mixture was then stirred under reflux for 30 minutes and cooled overnight. It was then reheated to reflux, and about 22 ml. of butanol and water was distilled away. The mixture was then cooled again, and diluted with about 50 ml. of water. The aqueous layer was separated and extracted with three 25 ml. portions of dichloromethane. The organic layers were combined, washed with 1 N sodium hydroxide, dried over sodium sulfate and evaporated under vacuum to obtain 3.0 g. of impure product. The product was dissolved in 30 ml. of dichloromethane, washed with water, dried over sodium sulfate and concentrated under vacuum again to obtain 2.67 g. of product, found to be 83% pure by vapor phase chromatography.

Example 9

Methyl 3-trifluoromethylphenylacetate

Fifty ml. of methanol, 4.9 g. of sodium hydroxide and 6.0 g. of 1,1,1-trichloro-2-(3-trifluoromethylphenyl)ethane were combined, and stirred under reflux for 6 hours. The mixture was cooled overnight, and was then made acid with 2.5 ml. of concentrated sulfuric acid. It was stirred under reflux for 1 hour more, cooled and filtered. The solids were washed with 100 ml. of methanol. Thirty ml. of water was added to the filtrate, and the aqueous layer was separated and washed 3 times with 20 ml. portions of dichloromethane. All of the organics were combined, and washed with two 15 ml. portions each of water and saturated sodium chloride. The organics were then dried over sodium sulfate and evaporated under vacuum to obtain 4.6 g. of an oil, which was found to contain 94% of the desired product by vapor phase chromatography.

The process was repeated, using a different lot of the trichloro compound, to obtain 4.3 g. of oil, 94% pure.

Example 10

Methyl (3-trifluoromethylphenyl)acetate

A 3.36 g. portion of flaked sodium hydroxide was slurried in 33 ml. of methanol and 1 ml. of water, and the mixture was warmed to dissolve most of the base. It was then cooled to ambient temperature and to it was added over 2–3 minutes 4 g. of 1,1,1-trichloro-2-(3-trifluoromethylphenyl)ethane. The mixture was then stirred under reflux at 70° for 4 hours, and was then cooled to 5°. To it was added about 3 ml. of concentrated sulfuric acid. A little more methanol was added to increase the fluidity of the mixture, and the mixture was stirred under reflux again for 45 minutes more. It was then cooled to ambient temperature, and diluted with about 60 ml. of water. A 35 ml. portion of dichloromethane was added, the layers were separated, and the aqueous layer was extracted with three 25 ml. portions of dichloromethane. All of the organics were combined and washed twice with 15 ml. portions of water, dried over sodium sulfate and concentrated to dryness under vacuum to obtain 2.75 g. of product, found to be 80% pure by vapor phase chromatography.

Example 11

Butyl (3-trifluoromethylphenyl)acetate

To a suspension of 5.6 g. of potassium hydroxide, containing 14% of water, in 35 ml. of dried butanol was added 4.0 g. of 1,1,1-trichloro-2-(3-trifluoromethylphenyl)ethane over about 2 minutes. The mixture was stirred under reflux for 5 hours, was cooled, and was made acid with 6 ml. of concentrated sulfuric acid. The mixture was heated to reflux with a distillation head on the flask, and about 11 ml. of butanol-water azeotrope was removed. Ten ml. of butanol was added back to the flask, and the mixture was cooled overnight to ambient temperature. It was then poured into 150 ml. of water, and the aqueous layer was extracted with two 40 ml. portions of dichloromethane. The organics were combined, and washed twice with 30 ml. portions of water. The organics were then dried over sodium sulfate, and concentrated under vacuum to obtain 4.0 g. of oily product, which was redissolved in 30 ml. of dichloromethane and washed twice with 10 ml. portions of water. The organic solution was dried over sodium sulfate and evaporated under vacuum to obtain 3.4 g. of product, found to be 94.5% pure by vapor phase chromatography.

Example 12

Methyl (3-trifluoromethylphenyl)acetate

Seventy ml. of methanol was combined with 10.7 g. of 86% pure potassium hydroxide and the mixture was stirred for 0.5 hour. To it was added 8.0 g. of 1,1,1-trichloro-2-(3-trifluoromethylphenyl)ethane over 3–4 minutes. The mixture was heated and stirred under reflux at 68° for 4.75 hours, cooled to 10° and made acid with 8 ml. of concentrated sulfuric acid. The mixture was then stirred under reflux for 45 minutes more, and cooled to ambient temperature overnight. To it was then added 100 ml. of water and 50 ml. of dichloromethane. The aqueous layer was extracted with two 40 ml. portions of dichloromethane, and the organics were combined, dried over sodium sulfate and concentrated under vacuum to obtain 5.7 g. of brown oil, found to be 96.6% pure product by vapor phase chromatography.

The product was further purified by distillation at 70°–73° under 1.3 torr to obtain 4.89 g. of more highly purified product.

Example 13

Methyl (3-trifluoromethylphenyl) acetate

Eight g. of potassium hydroxide of the grade used in the example above was dissolved in 20 ml. of methanol, and to it was added 25 ml. of toluene and 6.0 g. of 1,1,1-trichloro-2-(3-trifluoromethylphenyl)ethane. The mixture was then stirred under reflux for 6 hours, and was then allowed to cool to ambient temperature. It was made acid by the addition of 5 ml. of concentrated sulfuric acid, and was stirred under reflux for 1 hour more, at 69°. The mixture was then cooled and filtered, and the filter cake was washed with about 50 ml. of methanol. Fifty ml. of water was added to the filtrate, and the layers were separated. The aqueous layer was filtered and washed with 30 ml. of toluene, and the organic layers were combined. The organics were then washed with 50 ml. each of water and of saturated sodium chloride solution, and dried over sodium sulfate. The organic solution was then evaporated under vacuum to obtain 4.2 g. of yellow oil, which was found by vapor phase chromatography to be the desired product in 96% purity.

The following preparations illustrate the use of a typical product of the process of this invention.

Preparation 1

1-Cyano-1-phenyl-3-(3-trifluoromethylphenyl)-2-propanone

To a flame-dried flask was added 8.1 g. of sodium methoxide, 125 ml. of toluene and 21 ml. of methanol. The mixture was brought to reflux at 85°–87°, and to it was added dropwise a mixture of 22.8 g. of methyl (3-trifluoromethylphenyl)acetate and 12.9 g. of phenylacetonitrile. The apparatus was then set up for distillation, and the mixture was heated to 110°, removing about 46 ml. of distillate. The mixture was then cooled to about 12°, and to it was added 50 ml. of ice-water. The aqueous layer was removed and washed with 20 ml. of cold toluene. The organics were combined and washed with cold water. The aqueous layers were combined, and the pH was adjusted to 3.5 with cold hydrochloric acid. The oily product was collected by extracting the aqueous portion with three 40 ml. portions of dichloromethane, drying the organic layer over sodium sulfate and evaporating it under vacuum to obtain 30.5 g. of oil, which was 89% pure product by vapor phase chromatography.

Preparation 2

1-Phenyl-3-(3-trifluoromethylphenyl)-2-propanone

A 4.28 g. portion of the product of Preparation 1, 12 ml. of glacial acetic acid, 4 ml. of concentrated sulfuric acid and 4 ml. of water were combined and heated carefully to reflux at 116°, held at that temperature for 3.5 hours, and then extracted with 35 ml. of toluene. The aqueous layer was washed twice with 15 ml. portions of toluene, and all of the organic layers were combined and washed once with water. The organics were then added to 20 ml. of 5% sodium carbonate solution and stirred for 2 hours. The organic layer was then separated, washed with water, dried over sodium sulfate and evaporated to dryness under vacuum to obtain 3.42 g. of oily product, found to be 93% pure by vapor phase chromatography.

I claim:

1. A process for preparing a phenylacetate of the formula

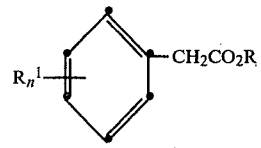

wherein

R is $C_1$–$C_6$ primary or secondary alkyl or $C_3$–$C_6$ cycloalkyl; the $R^1$ groups are independently chloro, fluoro, bromo, iodo, $C_1$–$C_3$ alkyl, $C_1$–$C_3$ alkoxy, nitro, or trifluoromethyl;

n is 0–3, provided that n is 3 only when the $R^1$ groups are chloro or bromo;

comprising hydrolysing a trichloro compound of the formula

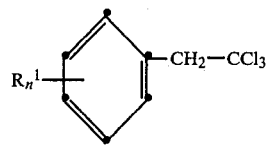

with sodium or potassium hydroxide in the presence of an alcohol of the formula ROH.

2. A process of claim 1 for preparing a phenylacetate wherein R is an alkyl group.

3. A process of claim 2 for preparing a phenylacetate wherein R is a primary alkyl group.

4. A process of claim 2 for preparing a phenylacetate wherein n is 1.

5. A process of claim 3 for preparing a phenylacetate wherein n is 1.

6. A process of claim 4 for preparing a phenylacetate wherein $R^1$ is trifluoromethyl.

7. A process of claim 5 for preparing a phenylacetate wherein $R^1$ is trifluoromethyl.

8. A process of claim 2 for preparing a phenylacetate wherein the $R^1$ groups are independently chloro, fluoro or bromo.

9. A process of claim 3 wherein the $R^1$ groups are independently chloro, fluoro or bromo.

10. A process of claim 7 for preparing a phenylacetate wherein R is methyl or butyl.

11. A process of any one of claims 1–10 wherein the hydrolysis is done with potassium hydroxide.

12. A process of claim 11 wherein no solvent except the alcohol is present.

13. A process of claim 12 wherein the hydrolysis is in the presence of a small amount of water.

14. A process of claim 13 wherein the temperature is about the reflux temperature at ambient pressure.

* * * * *